United States Patent [19]

Bernstein et al.

[11] Patent Number: 5,163,421

[45] Date of Patent: Nov. 17, 1992

[54] IN VIVO ULTRASONIC SYSTEM WITH ANGIOPLASTY AND ULTRASONIC CONTRAST IMAGING

[75] Inventors: Jonathan Bernstein, Tel Aviv; Uri Rosenschein, Ramat Hasharon, both of Israel

[73] Assignee: Angiosonics, Inc., Wayne, N.J.

[21] Appl. No.: 449,465

[22] Filed: Dec. 12, 1989

Related U.S. Application Data

[63] Continuation of Ser. No. 215,981, Jul. 7, 1988, abandoned, which is a continuation-in-part of Ser. No. 146,856, Jan. 22, 1988, abandoned.

[51] Int. Cl.$^5$ .............................................. A61H 21/00
[52] U.S. Cl. .................... 128/24.1; 606/159; 606/169
[58] Field of Search ............... 606/128, 170, 169, 159; 128/660.02–662.04, 24 A; 73/37, 575, 607, 623, 641

[56] References Cited

U.S. PATENT DOCUMENTS

| | | | |
|---|---|---|---|
| 3,352,203 | 11/1967 | Delaney | 128/24 A |
| 3,565,062 | 2/1971 | Kuris | 128/24 A |
| 3,861,391 | 1/1975 | Antonevich et al. | 128/24 A |
| 4,431,006 | 2/1984 | Trimmer et al. | 128/24 A |
| 4,587,958 | 5/1986 | Noguchi et al. | 128/24 A |

OTHER PUBLICATIONS

Neppiras et al., "Very High Energy Ultrasonics", *British Journal of Applied Physics*, vol. II (Apr. 1960).

*Primary Examiner*—C. Fred Rosenbaum
*Assistant Examiner*—William W. Lewis
*Attorney, Agent, or Firm*—Curtis, Morris & Safford

[57] ABSTRACT

An instrument and method for removing an obstruction from a human body lumen, such as an artery, is provided wherein the distal end of an ultrasonic transmission member is inserted within the artery and is connected at its proximal end to an ultrasonic power generator including a horn. A high efficiency ultrasonic transmission wire is connected to the horn which is formed from a material having a mechanical Q greater than about 50,000.

22 Claims, 3 Drawing Sheets

IN VIVO ULTRASONIC SYSTEM WITH ANGIOPLASTY AND ULTRASONIC CONTRAST IMAGING

This is a continuation of U.S. application Ser. No. 215,981, filed Jul. 7, 1988 now abandoned, which in turn is continuation-in-part of U.S. application Ser. No. 146,856, filed Jan. 22, 1988, now abandoned.

BACKGROUND

1. Field of the Invention

The invention relates to an apparatus and method for in vivo ultrasonic angioplasty. The apparatus of the invention may also be employed in an ultrasonic imaging system wherein it is used to generate acoustical contrast medium in situ.

2. Related Art

Arterial occlusions formed by thrombi and/or plaque deposits pose a serious threat to health. These deposits can result in a decrease or total blockage of circulation and lead to such conditions as peripheral vascular disease, angina pectoris and heart attack.

There are various known surgical techniques which may be employed to eliminate such occlusions, including replacement of the affected section of artery. Much work has been done toward development of non-surgical techniques in order to reduce the concomitant risk and trauma to the patient.

For example, one of the first non-surgical techniques developed was the balloon catheter which can be advanced into the circulation to dilate narrowed arteries. Such balloon catheters are well adapted for percutaneous insertion into the patient. This treatment method is generally referred to as "percutaneous transluminal angioplasty".

However, the unpredictable problems of abrupt closure and late restenosis of the dilated segment continue to compromise the overall results obtained with percutaneous transluminal angioplasty. High restenosis rates after coronary angioplasty of approximately 33%, and in multivessel angioplasty of approximately 68%, diminish the overall value of this technique even when one considers the low morbidity associated with the procedure. In addition, morphological studies indicate that the clinical improvement resulting from percutaneous transluminal angioplasty is accompanied by only a small increase in the diameter of the occluded artery. The mechanism of successful angioplasty involves internal disruption in fracturing of the atherosclerotic plaque with splits extending to the media an through it. Both splits and fractured plaques resulting from the angioplasty were later found to have been repaired by clots formed thereon. The relatively small channel reopened by percutaneous transluminal angioplasty combined with the injury caused to the arterial wall may account for the high re-occlusion rate. The high rates of early and late re-occlusion after peripheral and coronary angioplasty thus appear to be independent of the operator's skill and the quality of equipment but, rather, inherent in the procedure itself. There is accordingly great interest in either improving or finding alternatives to balloon-based systems and procedures.

The alternative to balloon angioplasty which has been most intensively researched to date—the laser-based angioplasty systems—offer the apparent ability to open a cleaner, wider channel by evaporation of plaque and thrombi. Laser excision of pathological tissue is, however, limited by the operator's ability to precisely control the depth of ablation and limit thermal injury to the target tissue. To date, the use of lasers in this manner has remained largely experimental, with the high rate of arterial perforation being the major practical limitation.

The concept of using acoustic energy for vascular intervention has been known for over twenty years. Early researchers noted that ultrasound could destroy atherosclerotic plaque and thrombi while leaving the underlying healthy vascular tissue undamaged. Experience with ultrasonic scalpel surgery has demonstrated that healthy vascular tissue is particularly resistant to ultrasonic energy. Recently, attention has once again been focused on the potential of ultrasound in vascular intervention. However, two problems have heretofore hindered the development of practical ultrasound systems for percutaneous insertion. First, since the ultrasound generator must be located outside of the body, it is often necessary to transmit the ultrasonic acoustic energy over a relatively long distance of 25 to 50 centimeters or more in order to pinpoint this energy at the site of the arterial occlusion. Attenuation of the acoustic energy along the length of the transmission member thus results in a loss of efficiency for the system, reducing the energy that reaches the internal arterial site. This requires the delivery of greater amounts of acoustical energy by the ultrasonic generator which rapidly increases fatigue of the transmission member.

A second problem is that this attenuation of acoustical energy is manifested as heat. Thus, the transmission member—which is primarily disposed within the circulatory system of the patient during treatment—can heat up rapidly during operation. Such heating can have serious adverse effects on the patient—a rise in the temperature of the transmission member of as little as 10° C., or less, can have serious deleterious effects. This limitation severely restricts the duration of time during which acoustical energy can be applied and also limits the amount of power which can safely be applied to the transmission member by the ultrasound generator.

Still another problem inherent in the use of any percutaneous technique is the ability to accurately position the tool, whether it be a balloon, a laser or an ultrasound transmission member, at the site of the occlusion.

U.S. Pat. No. 3,352,303 of Delaney teaches a method for blood clot lysis using a probe-catheter apparatus which generates vibrational wave energy at its tip. According to this patent, blood clots may be lysed by direct application of acoustical energy for short periods of time. However, a disadvantage of this method is that the time duration of application must be so short that the heating effects normally associated with the application of concentrated wave energy to the human body do not present a significant problem. Time durations of from 0.5 to 5 seconds are described. The probe or transmission member is constructed of either stainless steel or monel metal.

The apparatus according to U.S. Pat. No. 3,352,303 may also include optional means for introducing a radiopaque fluid via the catheter to locate the site of the thrombis and to position the catheter in relation thereto. Additionally, this apparatus may incorporate a further optional cooling fluid in the catheter for cooling the probe and, according to the patent disclosure, reducing losses in acoustical energy along the length of the probe.

U.S. Pat. No. 3,565,062 of Kuris describes an ultrasonic system for removing accumulations of cholesterol-bearing and other deposits from the circulatory system. In this patented system, ultrasonic energy is transmitted via a catheterized ultrasound transmission member to the site of the deposit. No specific materials of construction are disclosed for the transmission member. However, it is noted by the patentee that the transmission member will have a series of nodes or antinodes resulting during ultrasonic vibration. For prolonged of use, substantial heat is generated at the antinodes—periods so much that a red glow is visible at spaced apart locations. The patentee equates this heating with the loss in acoustical efficiency.

One way of overcoming such noticeable heating, according to the Kuris patent, is to continuously vary the ultrasonic frequency to shift the position of the nodes and antinodes. This procedure, however, does not overcome the problem of acoustical energy loss in the transmission member but, rather, merely serves to prevent the occurrence of localized overheating by spreading out the heat losses over the length of the member.

SUMMARY OF THE INVENTION

According to the present invention, an ultrasonic system for angioplasty includes an ultrasonic power generator, a high efficiency ultrasonic transmission member and, optionally, a catheter for housing the transmission member.

The high efficiency ultrasonic transmission member according to the invention must have a high mechanical Q (quality factor) so as to provide relatively little attenuation or dampening during ultrasound transmission. Preferably, the Q should be greater than about 50,000, and most preferably greater than about 100,000. The transmission member according to the invention is preferably constructed of aluminum or aluminum-based alloys which are utilized in their annealed or stress-relieved state to increase transmission efficiency. Particularly preferred aluminum based alloys are AL-7075, AL-2024 and AL-6061.

Preferably, the transmission member has a diameter of between about 0.8 to 1.6 millimeters. It is also preferable that the proximal end of the transmission member be flared to form an acoustic concentrator for attachment to the ultrasonic power generator. Preferably, the maximum outside diameter of the flared end should be about one-half inch. Additionally, in order to be utilized in a percutaneous insertion technique, the transmission member should preferably have sufficient flexibility to be passed through the patient's circulatory system and should be long enough to reach the site of the occlusion, preferably (but not exclusively) in the range of at least about 12.5 centimeters and preferably equal to an integral multiple of about one-half wave length of the ultrasound to about 125 centimeters.

The ultrasonic power generator should preferably have a frequency of operation between about 10 kilohertz and 100 kilohertz, most preferably about 20 kilohertz. Preferably, the ultrasonic power generator has a variable duty cycle to facilitate generation of pulsed ultrasound. Also, according to the preferred embodiment, the ultrasonic power generator is capable of delivering at least about 5 to 15 watts in output power.

In a preferred embodiment, the high efficiency ultrasonic transmission member and catheter, together, are adapted for percutaneous insertion into a patient. For use in a percutaneous insertion technique, the catheter is preferably constructed to have relatively little resistance to passage through the circulatory system of the patient and is compatible with blood. Preferably, the catheter is constructed of polyethylene or polyurethane, most preferably polytetraflouroethylene (Teflon).

In particular, the invention provides long flexible ultrasonic transmission members for the highly efficient transmission of high power ultrasonic energy.

The present invention also provides a method for ultrasonic angioplasty which comprises introducing an ultrasonic transmission member as described above into the circulatory system of the patient via a surgical or, preferably, a nonsurgical percutaneous insertion technique; maneuvering the tip of the transmission member to a point at or near the site of the occlusion to be treated; and applying ultrasonic energy, preferably pulsed ultrasound, thereto, at an intensity and for a duration sufficient to substantially break up the occlusion and recanalize the patient's artery to restore good blood flow therethrough.

In like manner, the ultrasonic apparatus according to the invention can be used for the removal of other obstructions, such as urinary tract obstructions and malignant tissue ablations in cavities such as the bladder, as well as for lysis of pulmonary emboli.

In an especially preferred method according to the invention, the ultrasonic transmission member is used to generate ultrasound contrast medium in situ. During transmission of ultrasound energy, ultrasonic vibrations at the tip of the ultrasound transmission member generate microbubbles in the patient's bloodstream. These microbubbles are visualized by a conventional ultrasound echo imaging system using contrast imaging wherein the microbubbles appear as a contrast medium. The ultrasound echo imaging in accordance with the invention is used to monitor the position of the tip of the ultrasound transmission member, to observe the progress of occlusion breakup, and/or to confirm the return of good blood flow past the site of the treated occlusion following treatment.

Further features and advantages of the present invention will be more fully appreciated by reference to the following detailed description of presently preferred, but nonetheless illustrative, embodiments in accordance with the invention when taken in conjunction with the accompanying drawings.

BRIEF DESCRIPTION OF THE DRAWINGS

In the drawings, wherein like reference numerals identify similar elements through the several views.

DESCRIPTION OF THE PREFERRED EMBODIMENTS

Figure 1:
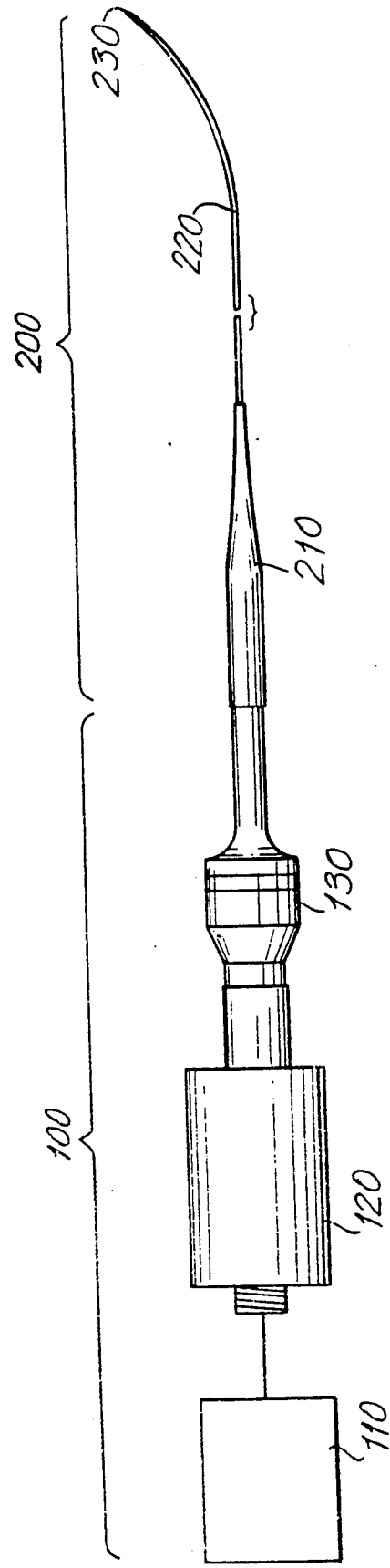
FIG. 1 is an elevated side view of an ultrasound apparatus in accordance with the present invention.

FIG. 1 depicts an ultrasound apparatus constructed in accordance with the present invention. From left to right are shown an ultrasonic power generator 100 including a frequency generator 110, a piezoelectric transducer converter 120 and a horn 130. The power generator 100, and/or parts thereof, may be conventional. Additionally, an ultrasonic transmission member 200 removably attached to generator 100 includes a microtip 210, a wire 220 and a distal end or tip 230.

The ultrasonic power generator 100 should preferably have an operating frequency between approximately 10 kilohertz to 100 kilohertz, and most preferably about 20 kilohertz. However, operating frequencies outside of this range may also be employed in accordance with the invention.

Additionally, the ultrasonic power generator 100 preferably has a variable duty cycle to facilitate generation of pulsed ultrasound. In accordance with a preferred embodiment of the invention, the generator 110 should be capable of delivering at least about 5 to 15 watts in output power.

A suitable ultrasound power generator for use in accordance with the invention is a Branson Sonifier Model B250 which operates at approximately 20 kilohertz for pulsed or continuous ultrasound.

Regarding the ultrasonic transmission member 200, the key parameter is the ultrasonic attenuation coefficient (also known as the ultrasonic damping or dampening factor) of the material from which it is constructed. The material must have a low coefficient to be useful in accordance with the present invention. The requirement that the transmission member 200 have a low attenuation coefficient can alternatively be expressed as a requirement for a high mechanical Q (quality factor).

In accordance with the invention, the transmission member is constructed of a metallic material. In selecting the metal of the ultrasonic transmission member or wire, it should be understood that all metals convert some of their vibrational energy into heat, resulting in an exponential attenuation of the ultrasound and heating of the wire. The longer the wire, the greater the loss and, consequently, the amount of heat generated. At lengths of 50 cm, the losses in most metal wires are sufficiently large that the wire will heat to the boiling point of water, and only a small fraction of the input mechanical energy is transmitted. This is clearly unacceptable.

The problem, then, is to find the right metal. Neppiras investigated the Q's of various metals, as part of a general research program having nothing to do with angioplasty. E. A. Neppiras, "Very High Energy Ultrasonics", British Journal of Applied Physics, Vol. II, April 1960, pp. 143–150. It has been found that the higher a metal's Q, the less energy is lost to heat when it vibrates and the lower the ultrasonic attenuation per unit length. The published results of Neppiras' investigation are as follows:

TABLE I

| Material | Mechanical Q |
| --- | --- |
| tool steel | 1,400 |
| naval brass | 3,000 |
| K-Monel | 5,300 |
| aluminum bronze | 17,000 |
| titanium | 24,000 |
| duralumin | >50,000 |
| hiduminium | >100,000 |

The mechanical Q of a particular metal varies with strain, frequency, temperature, and other factors. In Neppiras' method, Q is measured at F/2 and 20 KHz, where F equals the fatigue stress of the metal in dynes/cm$^2 \times 10^9$. The value of Q is deduced from calorimetric measurement of energy dissipation.

It has been found by the inventors that the absolute Q values reported by Neppiras can be used to broadly rank the suitability of metals for efficient transmission of ultrasound under angioplasty conditions. More particularly, the higher the Q, the more efficiently the material transmits ultrasound in accordance with the invention. From Table I it therefore appears that two aluminum alloys—duralumin and hiduminium—are more likely to more efficiently transmit ultrasound than the other metals there listed. (The chemical composition of hiduminium is very similar to that of aluminum 7075, which is readily available in bar form.)

Thus, in a preferred embodiment of the invention, the high-efficiency ultrasound transmission member is constructed of a material having a high mechanical Q value, preferably greater than about 50,000, and most preferably greater than about 100,000 as measured by the Neppiras method at F/2 and 20 KHz.

In accordance with the invention, a material having a high Q as measured by the Neppiras method at F/2 and 20 KHz will be suitable for use in a high-efficiency ultrasound transmission member over the entire range in frequency of operation of the ultrasound apparatus according to the invention.

Suitable materials of construction for the transmission member include aluminum or aluminum-based alloys having the desired Q value and which are preferably utilized in their annealed or stress-relieved state. Indeed, it has been found that aluminum-based alloys are the most preferred materials for the ultrasound transmission member of the invention. Persons having ordinary skill in the art will be able to select appropriate materials of construction in accordance with the present disclosure.

The act of drawing wire to form the transmission member creates imperfections in the metal's polycrystalline structure. These imperfections give the wire strength, but they also increase the ultrasonic attenuation due, it is currently believed, to internal friction and hysterisis (the general theory of damping due to these imperfections is called "dislocation damping"). It is therefore preferred that the wire 220 not be formed by drawing thereof but, rather, that the wire 220 and microtip 210 be formed from a single bar or rod of material which is lathed. Whether the wire is drawn, or lathed from a bar of material, however, it is most preferred that it be heat treated to remove or reduce imperfections in the material and increase transmission efficiency.

Thus in a preferred embodiment of the invention, the aluminum (or other metal) forming the wire should be in either its annealed or a stress-relieved state. The stress-relieved state is stronger than the annealed state but has more imperfections. However, it has been found by the inventors that both states work in accordance with the present invention. This can be achieved by heat treating the wire in a manner known to those of ordinary skill in the art of metallurgy.

Particularly preferred aluminum-based alloys for constructing the transmission member according to the invention are AL-7075, AL-2024 and AL-6061. In this regard, titanium, with a Q of only about 24,000, has been found by the inventors to have ultrasound attenuation characteristics too great to be satisfactorily useful as the material of construction of the transmission member in accordance with the present invention.

Preferably, the ultrasound transmission member comprises a wire having an outside diameter B of between approximately 0.8 and 1.6 millimeters and a length that is preferably an integral multiple of about one-half wave length of the ultrasound being transmitted. One end of the wire is preferably integral with the microtip which flares into a one-half inch diameter termination (identified as diameter "A" in FIG. 2) for attachment to the ultrasonic generator 100. This flared section is the acoustic "concentrator" which achieves the impedance match between the wire and the generator. The impedance match is achieved by controlling the taper of the flared section, as is well known in the literature. The particular concentrator currently used, the Branson Microtip, is a "conical sectional concentrator". However, other taper profiles can also be used to achieve the impedance match. The concentrator and the wire are most preferably lathed from a single bar of metal so as to achieve a good match and to avoid using drawn wire. In accordance with the invention, the entire transmission member is heat treated to either anneal or stress relieve the metal.

The shape of the wire tip 230 has a strong influence on system performance. In accordance with the present invention, it is preferred that the wire tip be flat as it has been found by the inventors that a flat tip is substantially more effective in destroying plaque than when the tip 230 is rounded or of irregular shape as may result from cutting of the wire by a conventional wire cutter or pair of pliers. The peripheral edges of the wire tip 230 may be smoothed or rounded so as to avoid inadvertent perforation or damage to tissue as the transmission member is longitudinally advanced in, for example, an artery to the intended internal site. However, at least the remainder of the tip—i.e. the face of the wire tip 230 radially inward of the peripheral edge—should, preferably, be flat. It is considered to be within the ability of one having ordinary skill in the art to obtain a wire tip 230 which is flat.

Figure 2:
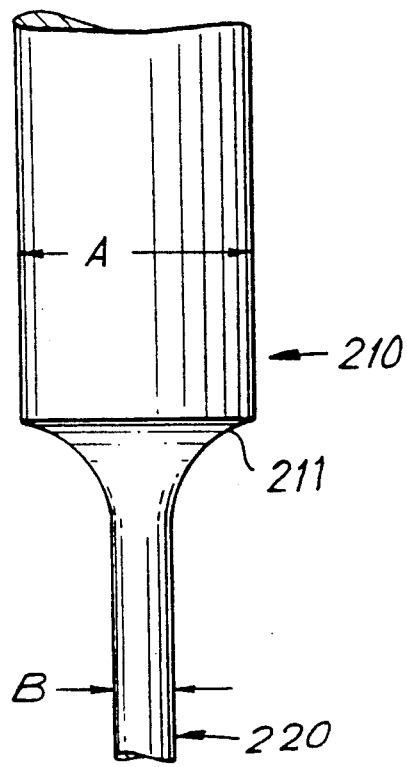
FIG. 2 is an elevated side view of a unitary microtip and wire transmission member lathed from a single bar.

Turning now to FIG. 2, a preferred embodiment of a unitary connection or junction between the microtip 210 and the wire 220 is illustrated. In this embodiment, the microtip 210 and wire 220 are lathed from a single bar or rod of material. The microtip 210 according to this preferred embodiment is in the basic form of a cone followed by an exponential taper 211. It is important that the junction between the microtip 210 and the wire 220 be constructed to enable the efficient transmission of ultrasound energy through the junction. While applicants have found a unitary connection between the microtip 210 and wire 220 to be preferred, and the particular unitary structure illustrated in FIG. 2 to be highly satisfactory, it is contemplated that other forms of joints and joint structures may be employed in accordance with the invention.

Figure 3:
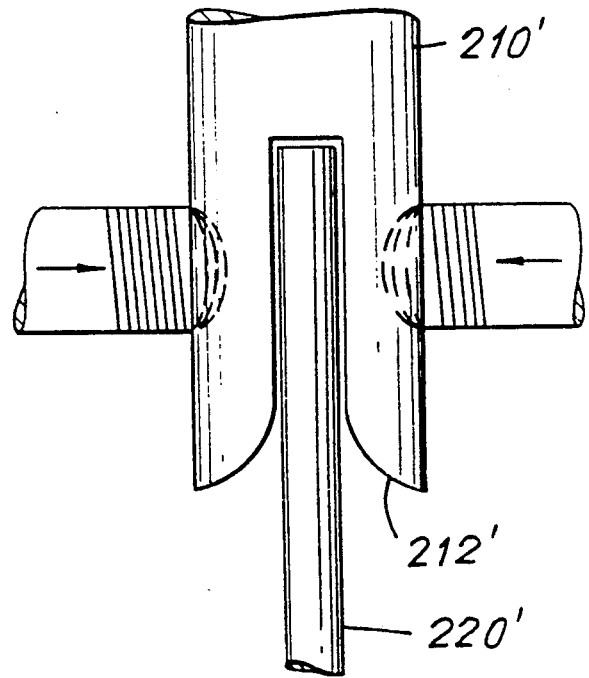
FIG. 3 is an elevated side view of a joint connecting a microtip and wire transmission member.

One such alternative structure is illustrated, by way of example, in FIG. 3. As there shown, the microtip 210' includes a bore defined therein and into which the proximal end of the wire 220' is inserted. Crushing force is then applied to the microtip 210', as indicated by the opposing arrows in FIG. 3, to securely retain the end of the wire 220' within the bore. In a joint of this type it is preferable that the open end of the bore 212' be curved or rounded.

Alternatively, the bore in the microtip 210' may have a slightly smaller diameter than the diameter of the wire 220'. Upon heating of the microtip 210', the bore will expand and the wire 220' can be inserted therein; when the microtip 210' cools, the wire 220' will be held firmly in place.

Figure 4:
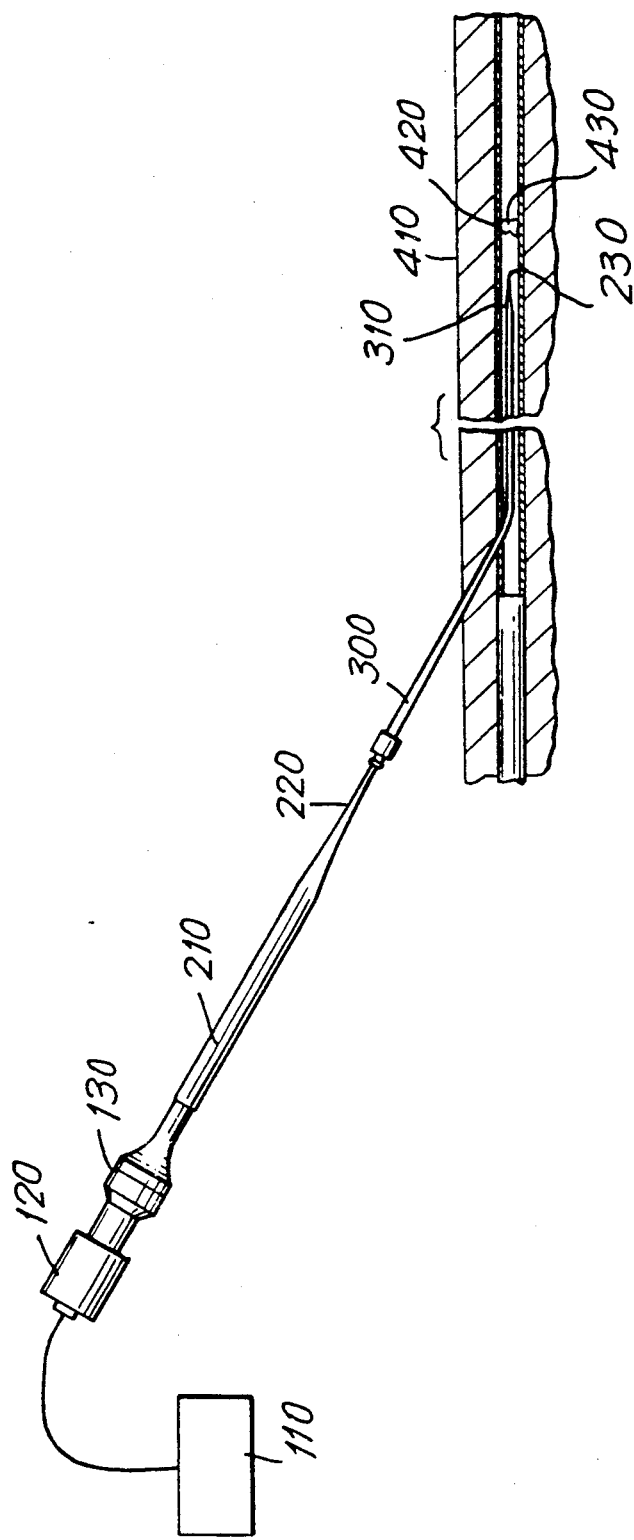
FIG. 4 is an elevated side view of an ultrasound apparatus according to the invention which is adapted for percutaneous insertion of at least a portion of the transmission member into a patient.

FIG. 4 depicts the ultrasound apparatus according to the invention adapted for percutaneous insertion of the ultrasound transmission member into a patient. As shown in FIG. 4, the wire 220 of the ultrasound transmission member is disposed within a catheter 300 and positioned for applying ultrasonic energy to target tissue 430 via the tip 230.

In this preferred embodiment, the high-efficiency ultrasonic transmission member 200 and catheter 300, together, are adapted for percutaneous insertion into a patient. In this regard, the wire 220 is located within the inner diameter of the catheter 300 and is longitudinally relatively slidable therewithin back and forth along the length of the catheter 300 between a retracted position for insertion and an extended position for operative use.

In the retracted position, the tip 230 of the wire 220 is either flush with or withdrawn inside the tip 310 of the catheter 300 to avoid puncturing or otherwise damaging the patient's artery and tissue during percutaneous insertion.

In the extended position, the tip 230 of the wire 200 is extended several millimeters out past the tip 310 of the catheter 300.

Preferably, the relative position of the tip 230 of wire 220 with respect to the tip 310 of catheter 300 is indicated by markings at least at or about the proximal end of wire 220—that end of the wire closest to the microtip 210.

The sheath or catheter 300 may be of any appropriate known form. For use in a percutaneous insertion technique, the catheter 300 may preferably be constructed in full or part of a material exhibiting relatively little resistance to passage through the circulatory system of the patient and suitably compatible with blood. Preferably, the catheter 300 is constructed of polyethylene or polyurethane. Most preferably, the catheter 300 is constructed of or coated with polytetraflouroethylene (Teflon).

It is further contemplated that the catheter 300 employed in the apparatus according to the invention may optionally include an irrigation channel or space between the wire 220 and the inside diameter of the catheter for contrast media injections and/or lubrication of the wire 220. It is also contemplated that an intravascular anchoring balloon to assist in holding the wire 220 in place during use may be incorporated at or near the tip 310 of catheter 300. In this regard, a three-foil balloon that will not appreciably obstruct blood flow is preferred.

The operation of the ultrasound apparatus according to the invention will now be described.

Referring once again to FIG. 4, the catheter 300 is inserted into the patient using a standard percutaneous insertion technique well known in the art. The wire 220 is then inserted into the catheter 300 and advanced until the wire tip 230 is within several millimeters of the catheter tip 310. Once the catheter tip 310 is positioned close to the obstruction or target tissue 430 in the patient's artery 420, the wire is advanced to extend the wire tip 230 several millimeters beyond the tip 310 of the catheter 300. Once so positioned, ultrasonic energy, preferably pulsed ultrasound, is applied via the tip 230 to the obstruction or target tissue 430 at an intensity and for a duration sufficient to substantially break up the target tissue 430 and recanalize the patient's artery to restore good blood flow therethrough.

Additionally, it is contemplated that the apparatus according to the invention be used to generate ultrasound contrast medium in situ for ultrasound echo imaging to monitor the progress and success of the ultrasound treatment in breaking up the target tissue 430. In this regard, during transmission of ultrasound energy, ultrasonic vibrations at the tip 230 of the ultrasound transmission member 200 generate microbubbles in the patient's bloodstream. These microbubbles are visualized by conventional ultrasound echo imaging systems wherein the microbubbles appear as a contrast medium. Those skilled in the art will recognize and appreciate the significant advantages realized in this manner by obviating any need to inject, as is conventional, a separate contrast medium into the bloodstream of the patient for X-ray imaging.

Following treatment of the target tissue 430, the ultrasound apparatus is withdrawn.

The following examples will further illustrate, by way of example, the invention.

METHODS

Ultrasonic angioplasty catheter

The apparatus employed for the following experiments comprised a flexible ultrasonic transmission wire housed in a No. 5F Teflon sheath wherein the wire was freely advanceable and retractable. Markings on the wire indicated its position relative to the sheath. The proximal end of the wire was attached to the ultrasonic power source (Branson Sonifier, Model B250) which was capable of generating 20 khz pulsed or continuous ultrasound; the front panel settings of the Sonifier were set at 30% duty cycle with a power setting of 1 to 2 for all experiments. Wire diameters of 1.0 mm and 1.6 mm and lengths of 12.5 cm, 25 cm, and 37.5 cm were employed.

Testing in vitro

Atherosclerotic plaque disruption: 31 aortic sections were removed from individuals who underwent postmortem examination within 24 hours of death and stored for less than 24 hours in 0.9% saline solution at a temperature of 4 degrees centigrade. The segments represented the full spectrum of gross appearance from normal through soft raised atherosclerotic lesions to complex lesions. The tip of the ultrasonic catheter—i.e. the ultrasonic energy-carrying wire—was placed in direct contact with each of 25 sections containing atherosclerotic plaques. Power was applied while the wire tip was swept over the entire area of the plaque until gross observation indicated that the plaque had either been entirely removed or had ceased to decrease in size. During application of ultrasound, the contact area was continuously irrigated with saline solution. Runoff was collected and examined microscopically using polarized light and contrast phase microscopy. Six healthy human aortic sections were exposed to ultrasound for 120 to 240 seconds.

All aortic segments exposed to ultrasound were placed in 10% neutral formalin. After fixation, two millimeter thick serial cross-sections of the aortic wall were embedded in paraffin and five micron thick sections were stained with eosin and hematoxylin, or with elastin.

Ultrasonic thrombolysis: Thrombus was formed by allowing 2.5 ml blood to stand for 4 to 6 hours in a test tube. 5 control and 5 test thrombi were studied. The wire tip was brought into contact with the thrombus and slight pressure was applied to penetrate the surface. In the test group, ultrasonic power was then applied for 20 to 30 seconds, during which time the wire was advanced through the thrombus 2 to 3 times. In the control group, no power was applied while the wire was advanced through the thrombus 2 to 3 times. Each thrombus, both control and test, was then centrifuged for 3 minutes at 2000 rpm and the liquid supernatant was separated from the residual solid thrombus. Thrombus was weighed before and after treatment. The liquid supernatant was microscopically examined.

Thrombus generation in vivo 11 mongrel dogs weighing 20 to 35 kg were studied. The dogs were divided into two groups on the basis of the monitoring equipment used: 4 dogs were hemodynamically monitored, while 7 dogs were studied angiographically.

Hemodynamically monitored group: General anesthesia was induced by phenobarbital. After surgical exposure of both femoral arteries, direct pressure tracings were obtained from each artery distal to the site of intended occlusion. Thrombus was generated. The right femoral artery was used as test; a 3 to 4 cm length of intimal injury was achieved by balloon deendothilization and crushing with forceps. The proximal and distal ends of the injured segment were then temporarily ligated and thrombin was injected into the occluded segment. The trapped blood was allowed to clot for 90 to 120 minutes. The ties were then released and vessel occlusion was ascertained by reduced pulse pressure amplitude in the tracing. The left femoral artery was left unoccluded as a control.

Angiography group: 11 femoral arteries—7 test and 4 control—were occluded as described above. After ligation, stainless steel needles were inserted into the surrounding tissue at the ligation sites to serve as vascular markers that defined the extent of endothelial injury and occlusion during catheterization. After the ties were released, vessel occlusion was ascertained by hand injections of contrast material with 35 mm cine filming.

Ultrasonic thrombolysis protocol in vivo

Angiography group: After occlusion was verified angiographically, the ultrasonic angioplasty wire was introduced into the exposed femoral artery, approximately 15 to 20 cm distal to the occlusion. The wire was advanced to the site of occlusion and then forced 1–2 cm past the first vascular marker. Pulsed ultrasound was then applied for 2 minutes, during which time the wire tip was passed between the vascular markers 1 to 2 times. Ultrasound was applied only while the tip was between the two vascular markers. After application of ultrasound, recanalization was ascertained through injection of contrast media. In the control arteries, mechanical bridging of the occlusion was attempted. The wire tip, with ultrasonic power turned off, was advanced into the site of occlusion and remained there for 2 minutes, during which time it was passed back and forth between the vascular markers 1 to 2 times. Angiographic study was then repeated. Ultrasonic transmission wire diameter was 1.0 mm in one test vessel and one control vessel; all other experiments were conducted with 1.6 mm diameter wire. All cineangiograms were judged by two reviewers and were classified as:

1. total recanalization—restoration of $\geq 75\%$ of lumen diameter;
2. successful recanalization—reduction of obstruction by more than 25%; or
3. unsuccessful recanalization—no change from baseline.

Hemodynamic group: Once obstruction was verified by blood pressure tracing, introduction of the ultrasonic angioplasty wire into the femoral artery was performed as above. Mechanical bridging was attempted on the occluded right artery. The wire tip, with the ultrasonic power to the wire turned off, was advanced into the site of occlusion and remained there for 2 minutes, during which time it was passed back and forth between the vascular markers 1 to 2 times. The wire was withdrawn and blood pressure tracing recorded. The wire was then readvanced into the site and pulsed ultrasound applied for 1 minute. The wire was withdrawn and blood pressure tracing was recorded. The ultrasound application cycle was then repeated.

Successful recanalization in the test artery was defined as a restoration of blood pressure to 50% of blood pressure in the control artery.

In both groups, the animal was sacrificed immediately. Test and control arterial segments were removed and placed in 10% neutral formalin. After fixation, two millimeter thick serial cross-sections of the arterial wall were embedded in paraffin and five micron thick sections were stained with eosin and hematoxylin.

RESULTS

In vitro ultrasonic plaque disruption 25 atherosclerotic plaques were exposed to the ultrasonic angioplasty catheter. On gross observation, the plaque-bearing specimens showed dissolution of plaque with either total removal of plaque or crater formation within the plaque. There was variation in the rate at which plaques were disrupted. Soft fatty plaques dissolved most rapidly, while heavily calcified plaques were the most resistant to ultrasonic disruption. No gross damage was observed to healthy or normal tissue either underlying or adjacent to the plaque. Histological examination of sections showed n recognizable atherosclerotic plaque structure remaining. Residual plaque material was noted. The cellular architecture in the tissue adjacent to the area of ultrasound application remained intact. Runoff analysis showed the debris to be mainly cholesterol crystals and necrotic tissue remnants. The cholesterol crystals ranged in size from 10 to 80 microns in diameter; 90% of the crystals were less than 10 microns. Tissue remnants ranged in size from 50 to several hundred microns in diameter. Histological examination of the six healthy segments exposed to ultrasound showed no damage to the media or adventitia.

In vitro ultrasonic thrombolysis

Thrombolysis by the ultrasonic angioplasty catheter reduced solid thrombus weight from $1.56 \pm 0.15$ gr ($+1$ S.D.) to $0.35 \pm 0.08$ gr, while solid thrombus weight in the control group was reduced from $1.50 \pm 0.09$ gr to $1.26 \pm 0.12$ gr; average percent reduction in the test group was $76.9 \pm 5.1\%$ as compared to $15.8 + 5.8\%$ in the control group ($p < 0.0001$, $n=5$, students t test). Microscopic examination of the liquid supernatant showed 1 to 5 fibrin fragments per high power field. No re-coagulation of the liquid supernatant was noted after 60 minutes.

In vivo thrombolysis

Angiography group: Ultrasonic thrombolysis was attempted on test vessels with complete ($n=4$) or subtotal ($n=3$) occlusions. An additional 4 occluded vessels with complete ($n=1$) or subtotal ($n=3$) occlusion served as control. According to the recanalization criteria, 7 out of 7 test vessels were totally recanalized using the ultrasonic angioplasty catheter. Attempted bridging of thrombotic occlusions via mechanical penetration in 5 control vessels achieved total recanalization in no vessels, and successful recanalization in 1 vessel. 1 control vessel was mechanically perforated during attempted bridging. In the successfully mechanically recanalized vessel, a second channel through the partially occlusive thrombus was created by mechanical penetration; this channel decreased the obstruction by 30% to 40%.

Hemodynamically monitored group: In 3 of 4 test arteries successful recanalization was achieved after application of ultrasound, according to recanalization criterion.

Histology

Histological studies were carried out on 7 of the canine test arterial segments exposed to ultrasound in vivo and on 4 control canine arterial segments. In all sections examined, both test and control, damage to the intima and media was observed, while the adventitia appeared undamaged. Sections exposed to ultrasound did not show any greater histological damage than did the control sections. Intraluminal thrombi were present in all segments; test and control showed no difference in the extent of intraluminal thrombosis.

The ultrasonic angioplasty catheter according to the invention has proven to effectively induce thrombolysis. In vivo, the ultrasonic angioplasty catheter achieved total angiographic recanalization in 7 of 7 partially or completely thrombotically occluded canine femoral arterial segments. Furthermore, hemodynamic monitoring in an additional 4 dogs has shown ultrasonic angioplasty catheter to restore blood pressure in 3 out of 4 thrombotically occluded femoral arteries. Attempts to recanalize by purely mechanical penetration of thrombotic occlusion (using the wire with no ultrasonic power applied thereto) were unsuccessful, indicating that recanalization was primarily due to the effect of the ultrasound and not due to the mechanical penetration of the wire into the thrombus. Histologic studies showed intimal and medial damage in both the test and control canine arteries; there was no adventitial damage. That the test sections exposed to ultrasound showed no more damage than the control sections indicates that the intimal and medial damage observed may have been due to the injury caused by de-endolithization and crushing with forceps to induce thrombosis. In vitro, thrombolysis induced by the ultrasonic angioplasty catheter produced abundant fibrin fragments in the liquified portion of the thrombus, while reducing solid thrombus weight by 77% on average. The ultrasonic angioplasty catheter of the invention thus achieved effective in vivo thrombolysis with minimal damage to adjacent vascular tissue, presumably through selective destruction of the fibrin matrix in the thrombus.

The ultrasonic angioplasty catheter effectively disrupted 25 human atherosclerotic plaques. Fatty plaques were found to be the most sensitive to ultrasonic destruction, while heavily calcified plaques were the most resistant. Gross inspection as well a microscopic examination did not reveal damage to the vascular tissue underneath or adjacent to the area of exposure. Long exposures of healthy arterial wall segments to the ultrasonic angioplasty catheter of the invention did not produce histological damage.

The ultrasonic apparatus according to the invention destroys both plaques and thrombi while leaving healthy vascular tissue undamaged. Experience indicates that this selective destruction makes it user-friendly; there is no need for highly precise application of power since misdirection of the ultrasonic energy carrying wire does not result in damage to the healthy arterial wall. The potential advantage that ultrasonic angioplasty offers over alternative systems is that ultrasound exploits the inherent physical difference between the healthy arterial wall and the obstructive plaque-thrombus complex, allowing for selective destruction of only the luminal obstruction with no damage to the mechanical integrity of the vessel.

It should of course be understood that the foregoing examples are presented solely by way of example to illustrate the operation, use and advantageous benefits realizable in accordance with the present invention, and are not intended to serve as a limitation, either express or implied, on the apparatus or the method(s) of, or as to the scope of protection to be accorded, the invention. Thus, while there have been shown and described and pointed out fundamental novel features of the invention as applied to preferred embodiments thereof, it will be recognized and must be understood that various omissions and substitutions and changes in the form and details of the devices illustrated, and in their use and operation, may be made by those skilled in the art without departing from the spirit of the invention. It is the intention, therefore, to be limited only as indicated by the scope of the claims appended hereto.

We claim:

1. An ultrasonic system comprising an ultrasonic power generator including a horn, a high efficiency ultrasonic transmission wire connected to said horn, said high efficiency ultrasonic transmission wire being formed from a material having a mechanical Q greater than about 50,000.

2. A method for performing ultrasonic angioplasty using an ultrasonic system as set forth in claim 1, which comprises the steps of inserting the high efficiency ultrasonic transmission wire into the patient to be treated and then applying ultrasonic energy via the high efficiency ultrasonic transmission wire to an occulation in the patient's circulatory system for a duration and intensity effective for breaking up the occlusion and restoring good blood flow.

3. The ultrasound transmission system of claim 1, wherein said material from which said wire is formed is an aluminum based alloy.

4. The ultrasound transmission system of claim 3, wherein said aluminum based alloy is taken from the group consisting of duralumin, heduminium, AL-7075, AL-6061 and AL-2024.

5. A high efficiency ultrasound transmission member, comprising
   a wire which is formed from a material having a Q greater than about 50,000;
   connecting means for connecting the wire to the horn of an ultrasound generator.

6. The high efficiency ultrasound transmission member of claim 5, wherein the horn comprises a microtip and wherein the wire includes a flared end which is integral with the free end of said microtip.

7. The high efficiency ultrasonic transmission member of claim 6 wherein the wire has an outside diameter of about 0.8 to 1.6 millimeters which increase to about one-half inch in diameter at the flared end of the wire.

8. The high efficiency ultrasound transmission member of claim 7, wherein the wire has a free end surface which is flat at least one a face thereof which is radially inward of its outer periphery.

9. The high efficiency ultrasound transmission member of claim 5, wherein the wire has a free end surface which is flat at least on a face thereof which is radially inward of its outer periphery.

10. The ultrasound transmission member of claim 5, wherein said wire forming material is an aluminum based alloy.

11. The ultrasound transmission member of claim 10, wherein said aluminum based alloy is taken from the group consisting of duralumin, heduminium, AL-7075, AL-6061 and AL-2024.

12. A high efficiency ultrasound transmission wire that has been machined from a bar of material and is formed from a material having a mechanical Q greater than about 50,000, and a microtip of a horn connected to one end of said wire for transferring ultrasound thereto.

13. The ultrasound transmission wire of claim 12, wherein said wire and said microtip are machined as an integral assemblage from said bar of material.

14. The ultrasound transmission wire of claim 13, wherein the microtip at its end adjacent said wire is of substantially greater diameter than is said wire, and the transition from said end of said microtip to said wire is gradual.

15. The ultrasound transmission wire of claim 14, wherein said gradual transition is exponentially tapered.

16. The high efficiency ultrasound transmission wire of claim 12 which includes an end including a flat surface.

17. The high efficiency ultrasound transmission wire of claim 16, wherein said flat surface is surrounded by a peripheral portion that is rounded to reduce the likelihood of said wire perforating surrounding tissue.

18. An ultrasonic device for reducing an obstruction in a human body lumen defined by an anatomical wall, said device comprising:
   a. an ultrasonic power generator for generating ultrasonic energy, and ultrasonic power generator including:
      (i) an ultrasonic frequency electric wave generator,
      (ii) a transducer-converter for converting said ultrasonic frequency electric wave to an ultrasonic frequency mechanical wave, and
      (iii) a horn for altering the wave form of said ultrasonic frequency mechanical wave produced by said transducer-converter and for emitting said ultrasonic frequency mechanical wave from said ultrasonic power generator,
   b. an ultrasonic transmission wire having a proximal end connected to said horn and a distal end remote therefrom, said transmission wire being disposable within said human body lumen with said distal end adjacent said obstruction for transmitting ultrasonic mechanical energy from the horn of said ultrasonic generator to said obstruction without substantially altering the ultrasonic wave form applied to the proximal end thereof, to thereby reduce the size of said obstruction at said distal end,
   c. said transmission wire being made of a material having a mechanical Q of not less than about 50,000, whereby to permit the efficient transmission of ultrasonic energy through said transmission wire and to prevent said transmission wire when disposed in said lumen from heating up during the transmission of said ultrasonic energy to an extent that would injure said anatomical wall defining said lumen and any body fluid within said lumen.

19. The ultrasonic device of claim 18, wherein said human body lumen is a blood vessel.

20. The ultrasonic device of claim 19, wherein said blood vessel is an artery.

21. A method for transmitting ultrasound energy, particularly high power ultrasound, over a long flexible transmission wire, comprising transmitting the ultrasound energy using a long flexible transmission wire which is constructed of a material having a Q greater than about 50,000.

22. The method of claim 21, wherein the long flexible transmission wire has a length that is an integral multiple of about one-half wave length of the ultrasound to be transmitted and in the range of about 12.54 to about 125 centimeters.

* * * * *

UNITED STATES PATENT AND TRADEMARK OFFICE
CERTIFICATE OF CORRECTION

PATENT NO. : 5,163,421

DATED : November 17, 1992

INVENTOR(S) : Jonathan Bernstein et al.

It is certified that error appears in the above-identified patent and that said Letters Patent is hereby corrected as shown below:

Claim 2, line 6 (column 13, line 46), change "occulation" to --occlusion--.

Claim 7, line 3 (column 14, line 1), change "increase" to --increases--.

Claim 8, line 3 (column 14, line 5), change "one" to --on--.

Claim 18, line 5 (column 14, line 45), change "and" to --said--.

Claim 22, line 4 (column 16, line 10), change "12.54" to --12.5--.

Signed and Sealed this

Nineteenth Day of October, 1993

Attest:

BRUCE LEHMAN

*Attesting Officer*  *Commissioner of Patents and Trademarks*